United States Patent
Bottiglieri et al.

(10) Patent No.: US 9,360,768 B2
(45) Date of Patent: Jun. 7, 2016

(54) INSPECTION METHOD AND APPARATUS

(75) Inventors: Gerardo Bottiglieri, Veldhoven (NL); Elliott Gerard Mc Namara, Eindhoven (NL); Ruben Alvarez Sanchez, Veldhoven (NL)

(73) Assignee: ASML Netherlands B.V., Veldhoven (NL)

(*) Notice: Subject to any disclaimer, the term of this patent is extended or adjusted under 35 U.S.C. 154(b) by 868 days.

(21) Appl. No.: 13/482,323

(22) Filed: May 29, 2012

(65) Prior Publication Data

US 2012/0330592 A1 Dec. 27, 2012

Related U.S. Application Data

(60) Provisional application No. 61/499,401, filed on Jun. 21, 2011.

(51) Int. Cl.
| | |
|---|---|
| *G01N 21/47* | (2006.01) |
| *G01N 21/956* | (2006.01) |
| *G03F 7/20* | (2006.01) |
| *G06F 19/00* | (2011.01) |

(52) U.S. Cl.
CPC ............ *G03F 7/70625* (2013.01); *G01N 21/47* (2013.01); *G01N 21/956* (2013.01); *G03F 7/705* (2013.01); *G03F 7/70516* (2013.01); *G03F 7/70633* (2013.01); *G01N 2021/95615* (2013.01)

(58) Field of Classification Search
CPC .... G03F 7/705; G03F 7/70516; G03F 9/7019
See application file for complete search history.

(56) References Cited

U.S. PATENT DOCUMENTS

| | | | | |
|---|---|---|---|---|
| 6,795,193 | B2* | 9/2004 | Schulz | ........................ 356/445 |
| 2003/0187602 | A1 | 10/2003 | Bao et al. | |
| 2003/0187604 | A1 | 10/2003 | Drege et al. | |
| 2005/0185174 | A1* | 8/2005 | Laan et al. | ................. 356/243.1 |
| 2006/0166503 | A1* | 7/2006 | Sasaki et al. | .................. 438/692 |
| 2008/0049214 | A1* | 2/2008 | Maznev et al. | ................. 356/51 |
| 2008/0117437 | A1 | 5/2008 | Vuong et al. | |
| 2010/0081285 | A1* | 4/2010 | Chen et al. | ..................... 438/710 |

FOREIGN PATENT DOCUMENTS

| | | |
|---|---|---|
| EP | 1 628 164 A2 | 2/2006 |
| WO | WO 2010/069757 A1 | 6/2010 |

OTHER PUBLICATIONS

Written Opinion of the International Searching Authority with Search Report directed to related Int. App. No. PCT/EP2012/058889, mailed Oct. 19, 2012; 10 pages.

* cited by examiner

*Primary Examiner* — Manuel L Barbee
(74) *Attorney, Agent, or Firm* — Sterne, Kessler, Goldstein & Fox P.L.L.C.

(57) ABSTRACT

A method defines one or more monitoring target profiles, collects and stores initial calibration data of the metrology apparatus, compiling a library of spectra that would be observed from inspection of the monitoring target profiles using the metrology apparatus calibrated according to the initial calibration data. Some operations can be performed periodically, e.g., on a daily basis: obtaining current calibration data from the apparatus, modeling the effect of the current calibration data on the metrology apparatus operation, and using the result of the modeling and the contents of the library to determine any differences between one or more values of the initial calibration data and the current calibration data, and how these changes will be translated into changes in the measurement output for a given number of stacks and geometries.

17 Claims, 6 Drawing Sheets

Figure 1:
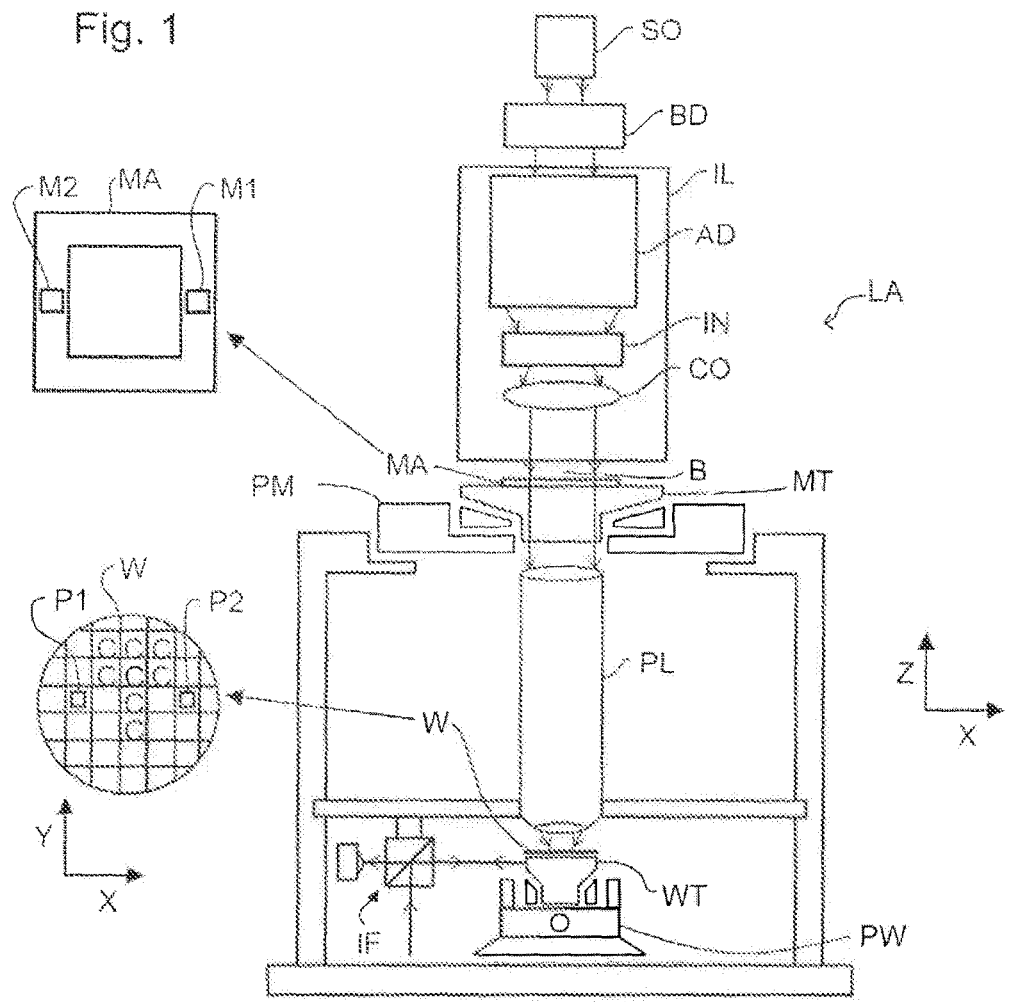

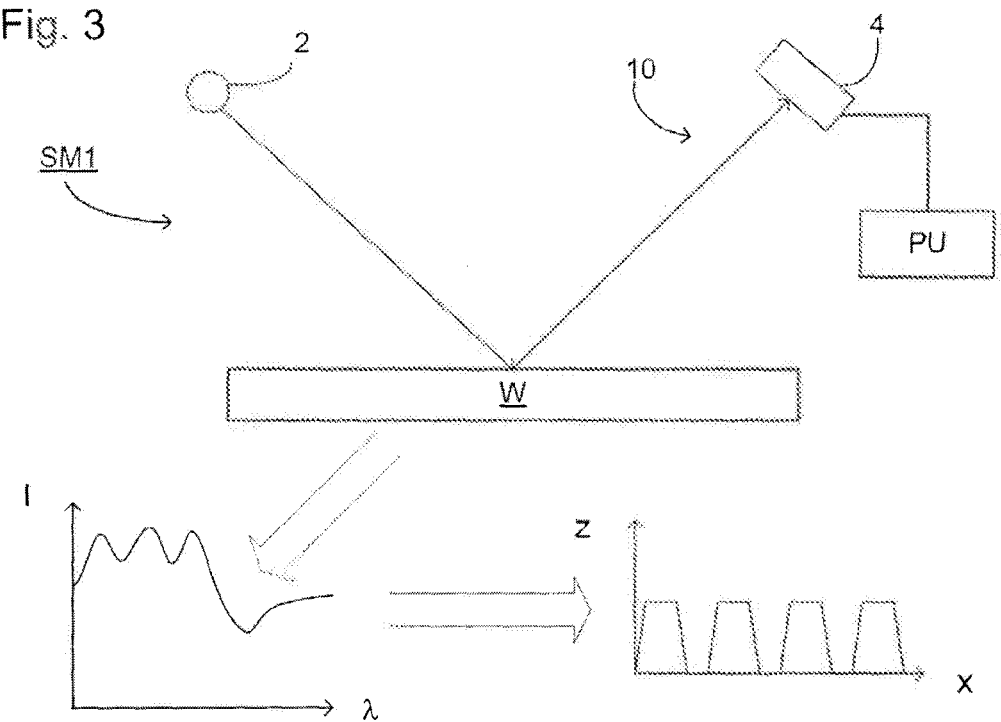
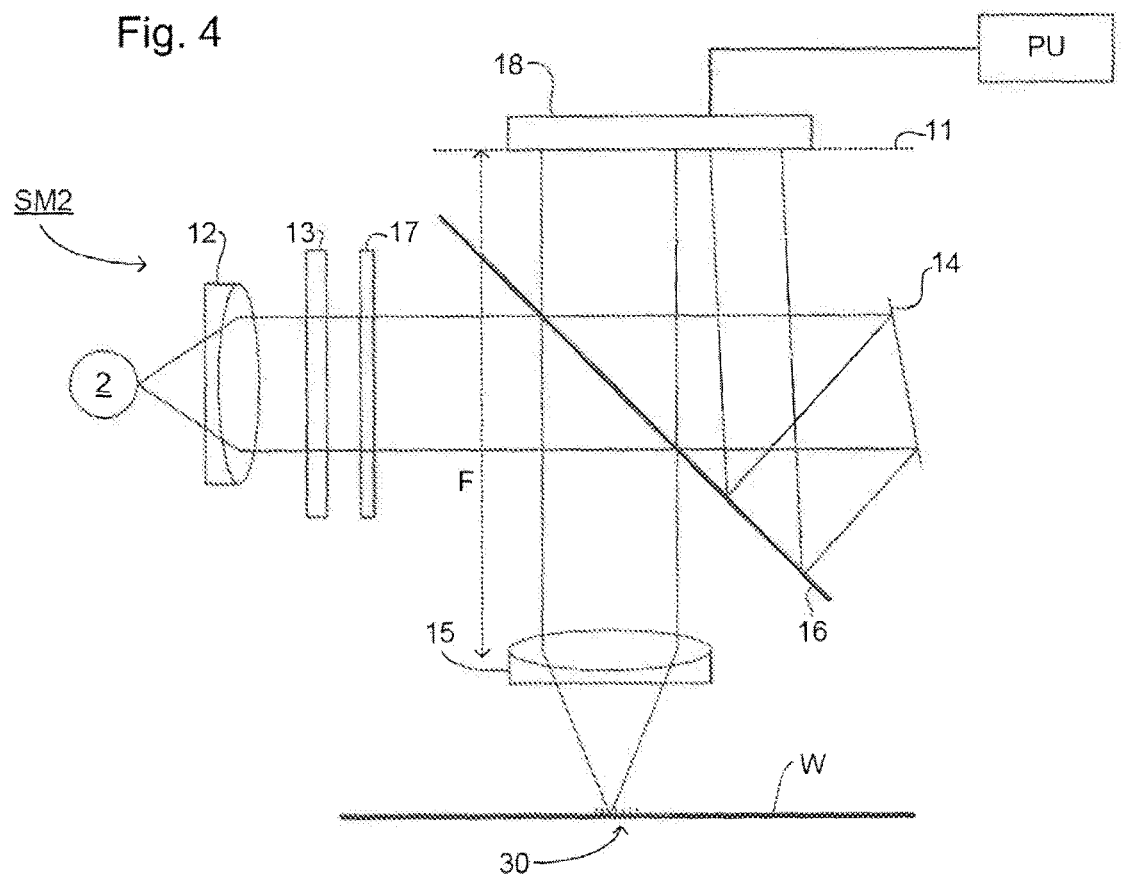

INSPECTION METHOD AND APPARATUS

CROSS REFERENCE TO RELATED APPLICATIONS

This application claims the benefit under 35 U.S.C. §119(e) to U.S. Provisional Patent Application No. 61/499,401, filed Jun. 21, 2011, which is incorporated by reference herein in its entirety.

BACKGROUND

1. Field of the Invention

The present invention relates to methods of inspection usable, for example, in the manufacture of devices by lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

It is very important for the output measurements of metrology tools to be stable, and therefore these output measurements should be accurately monitored. This can be done indirectly, for example by measurement of factors/system parameters likely to affect the output measurements. Or else direct monitoring of output measurements may be made by making measurements of actual physical target (e.g., reference wafers or in-built (fiducial) targets).

There are a number of drawbacks with either approach. Indirect monitoring relies on knowing exactly how the factors/system parameters being monitored, which is very difficult, if not impossible. Direct monitoring results in tool operations being interrupted to obtain the required measurements, while the target properties may change over time resulting in false indications of parameter instability.

BRIEF SUMMARY

It is an object of the present invention to address one or more of the problems inherent in the prior monitoring approaches discussed above.

According to an aspect of the invention, there is provided method of operating a metrology apparatus comprising defining one or more monitoring target profiles, collecting and storing initial calibration data of the metrology apparatus, compiling a library of spectra that would be observed from inspection of the monitoring target profiles using the metrology apparatus calibrated according to the initial calibration data, the method further comprising periodically performing the following steps: obtaining current calibration data from the apparatus, modeling a metrology measurement based on the current calibration data, and using the contents of the library to determine any differences between one or more values of the modeling parameters used in the modeling step, that are resultant from differences in the initial calibration data and the current calibration data.

Other aspects of the invention include a metrology apparatus and computer program product for carrying out this method.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 2:
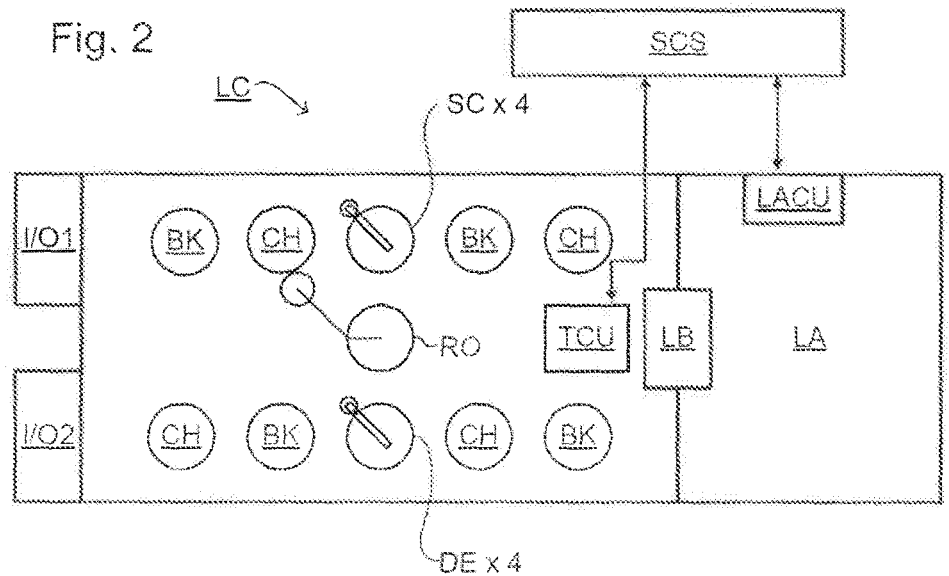
Figure 5:
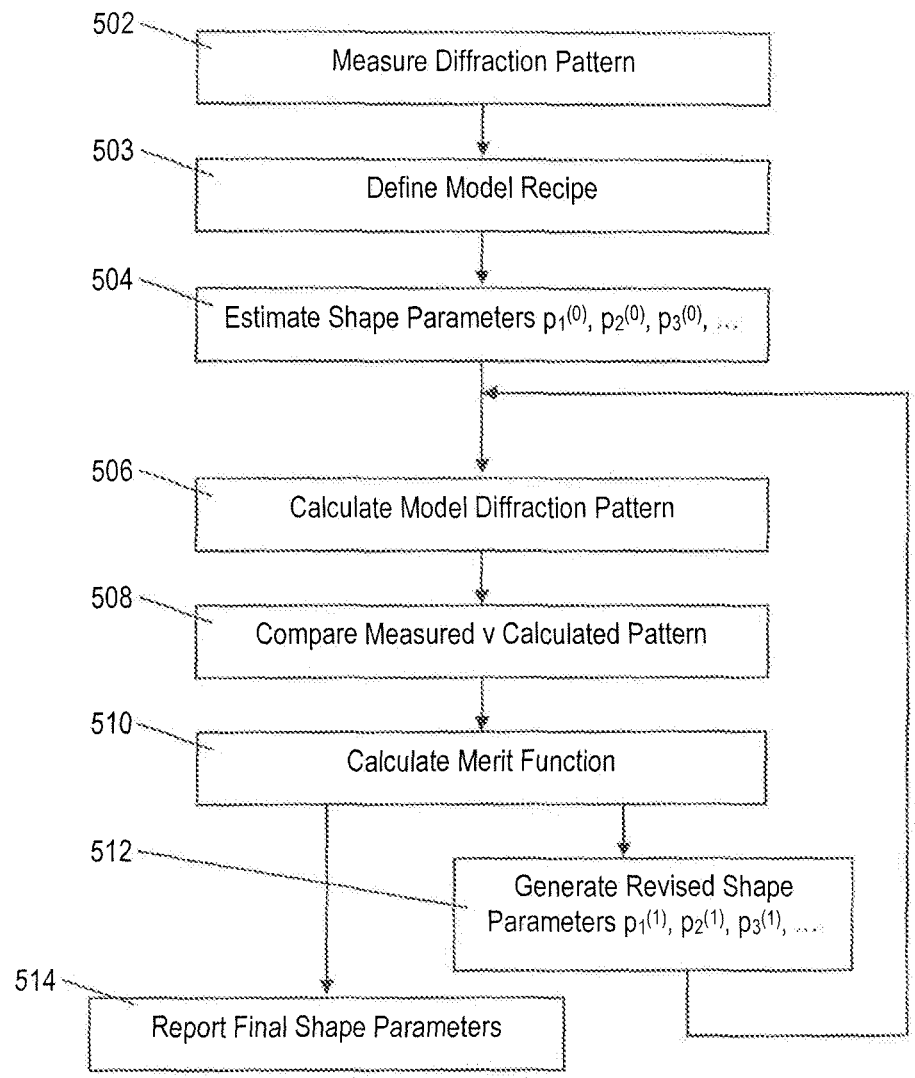
Figure 6:
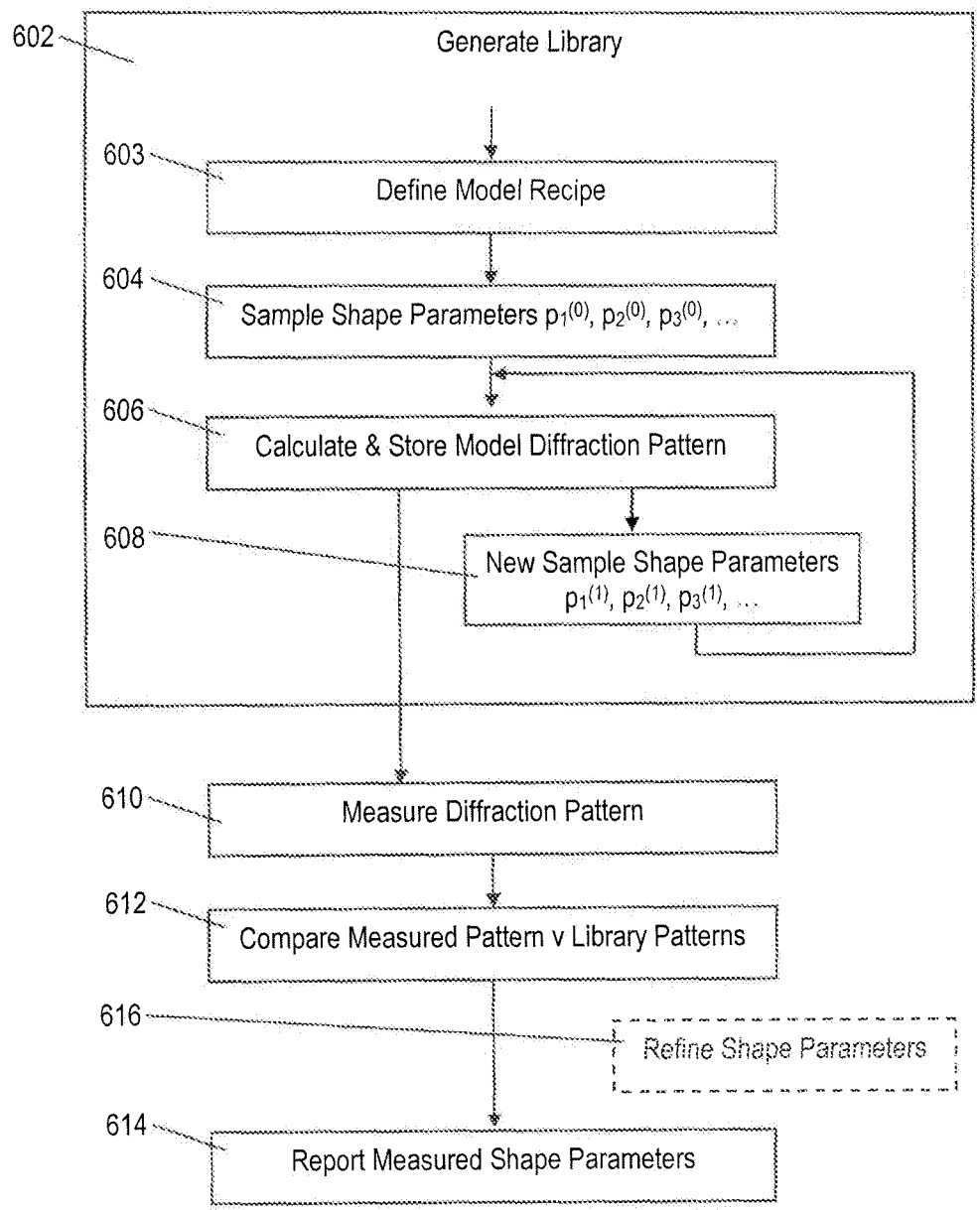
Figure 7A:
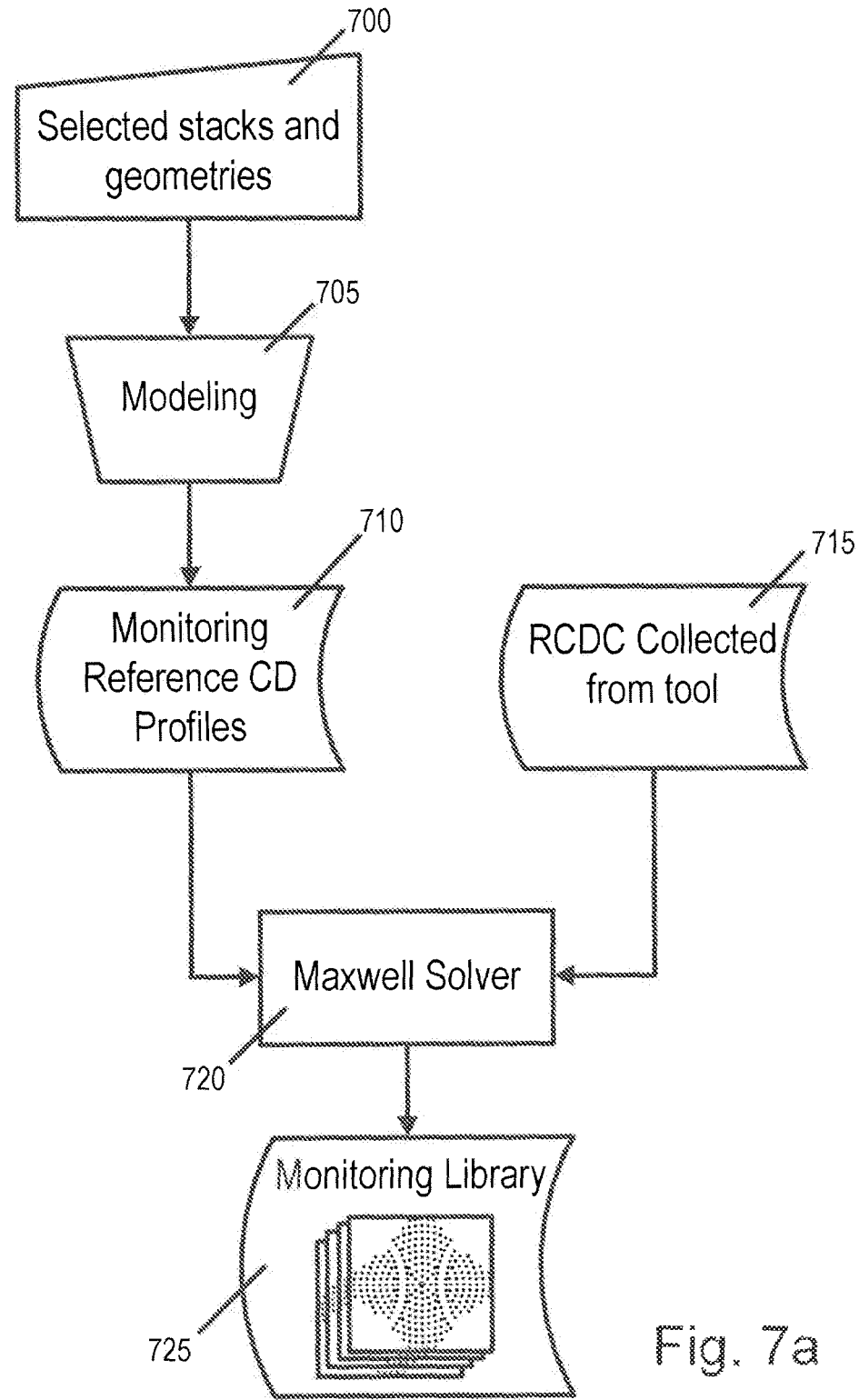
Figure 7B:
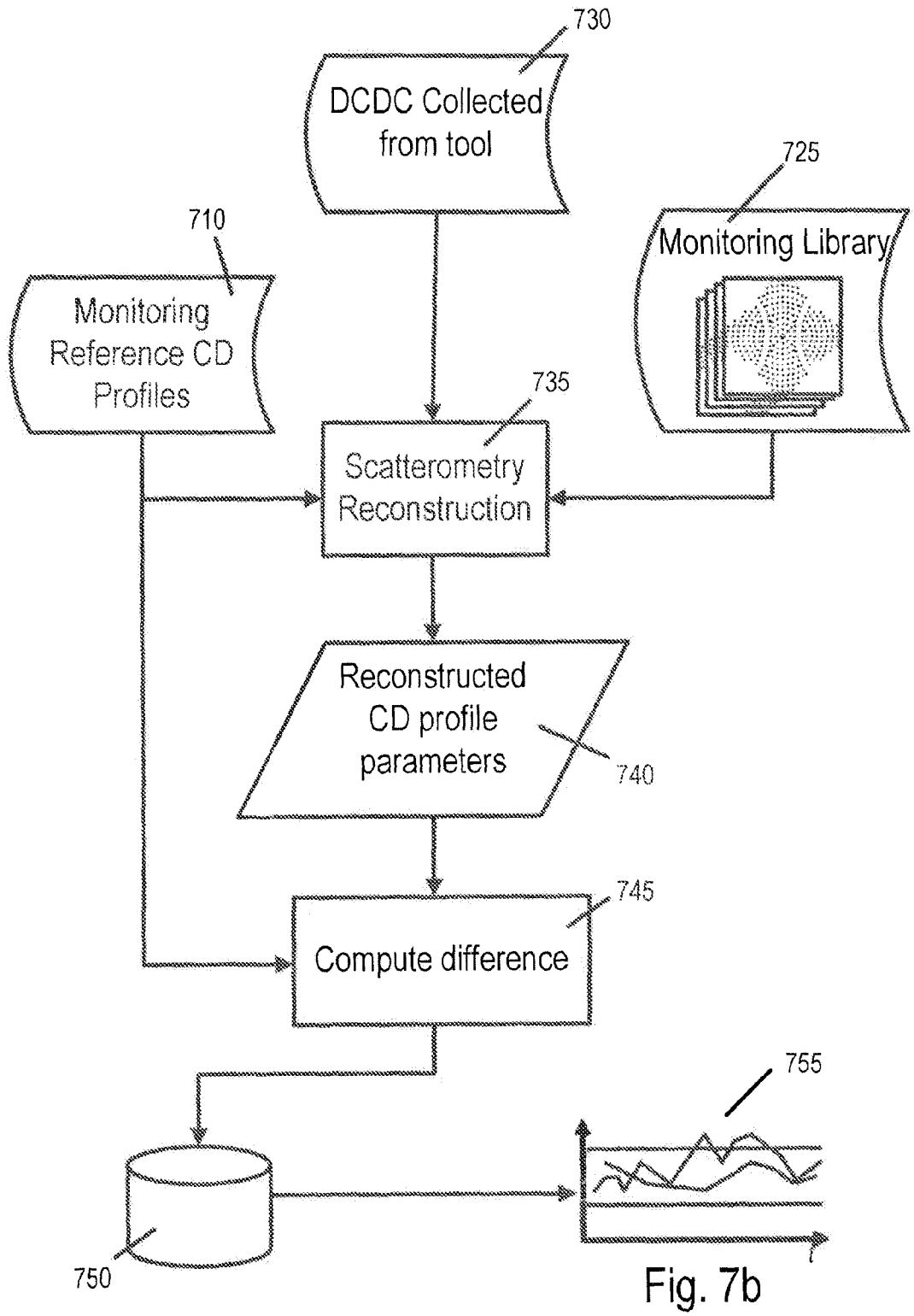

FIG. 1 depicts a lithographic apparatus.
FIG. 2 depicts a lithographic cell or cluster.
FIG. 3 depicts a first scatterometer.
FIG. 4 depicts a second scatterometer.
FIG. 5 depicts a first example process for reconstruction of a structure from scatterometer measurements.
FIG. 6 depicts a second example process for reconstruction of a structure from scatterometer measurements.
FIGS. 7a and 7b depict a process according to an embodiment of the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least $2\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the structure can be performed in a number of ways. In a first type of process, represented by FIG. 5, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Referring to FIG. 5 in more detail, the way the measurement of the target shape and/or material properties is carried out will be described in summary. The target will be assumed for this description to be periodic in only 1 direction (1-D structure). In practice it may be periodic in 2 directions (2-dimensional structure), and the processing will be adapted accordingly.

In step 502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503: A 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, ways will be introduced in which parameters can be permitted to vary without being fully independent floating parameters. For the purposes of describing FIG. 5, only the variable parameters are considered as parameters $p_i$.

In step 504: A model target shape is estimated by setting initial values $p_i^{(0)}$ for the floating parameters (i.e. $p_1^{(0)}$, $p_2^{(0)}$, $p_3^{(0)}$ and so on). Each floating parameter will be generated within certain predetermined ranges, as defined in the recipe.

506: The parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

In steps 508, 510: The measured diffraction pattern and the model diffraction pattern are then compared and their similarities and differences are used to calculate a "merit function" for the model target shape.

In step 512: Assuming that the merit function indicates that the model needs to be improved before it represents accurately the actual target shape, new parameters $p_1^{(1)}$, $p_2^{(1)}$, $p_3^{(1)}$, etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

In step 514: When the merit function indicates that this iterative process has converged on a solution with a desired accuracy, the currently estimated parameters are reported as the measurement of the actual target structure.

The computation time of this iterative process is largely determined by the forward diffraction model used, i.e., the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 502. For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5. The steps of the FIG. 6 process are:

In step 602: The process of generating the library begins. A separate library may be generated for each type of target structure. The library may be generated by a user of the measurement apparatus according to need, or may be pre-generated by a supplier of the apparatus.

In step 603: A 'model recipe' is established which defines a parameterized model of the target structure in terms of a number of parameters $p_i$ ($p_1$, $p_2$, $p_3$ and so on). Considerations are similar to those in step 503 of the iterative process.

In step 604: A first set of parameters $p_1^{(0)}$, $p_2^{(0)}$, $p_3^{(0)}$, etc. is generated, for example by generating random values of all the parameters, each within its expected range of values.

In step 606: A model diffraction pattern is calculated and stored in a library, representing the diffraction pattern expected from a target shape represented by the parameters.

In step 608: A new set of shape parameters $p_1^{(1)}$, $p_2^{(1)}$, $p_3^{(1)}$, etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610: After the library is generated (though it could be before), the real target 30 is placed in the scatterometer and its diffraction pattern is measured.

In step 612: The measured pattern is compared with the modeled patterns stored in the library to find the best matching pattern. The comparison may be made with every sample in the library, or a more systematic searching strategy may be employed, to reduce computational burden.

In step 614: If a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

In step 616: Optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e., the calculation of the estimated model diffraction pattern using a rigorous optical diffraction theory from the estimated target shape.

A key parameter for metrology tools is the stability of the output measurements. One possibility to monitor the measurement stability is to monitor several electrical/optical/mechanical/thermal/strain-stress/humidity (and so on) system parameters. This kind of monitoring is an indirect monitoring: it does not monitor directly the tool output, but all those variables which might influence such output. This approach has the advantage of not requiring any user intervention; it can be structurally implemented in the system by deploying several sensors in the most relevant parts of the system. Moreover it does not require any part or external tool which does not strictly belong to the system function, it is a continuous monitoring, and it does not interrupt normal tool operations (hence not reducing availability).

However, there are also a number of drawbacks to such indirect monitoring. Because metrology tools are complex systems, it is not possible to quantify the change in one or multiple monitored variables on the final output of the metrology tool, that is the measurement results (for example: mean critical dimension (MCD), side wall angle (SWA), thickness). For example, it is very difficult or impossible to quantify how much a certain change in the light intensity or humidity or temperature changes the measurement output. Moreover, the magnitude of the impact can be different for different layers (or for similar layers in different stacks) and therefore, even if the magnitude of the impact on one layer is known, it does not necessarily indicate anything about another layer nor about the same layer in another stack. Moreover, not only is the link between a certain variable and the tool output quantitatively unknown, but it is not necessarily the case that all the variables that have an impact on the output are known. Consequently, a user may see a change in the output of the tool without recording any change in the monitored variables.

An alternative monitoring approach is direct monitoring by dedicated measurement monitoring target(s). Such targets may be, for instance, the gratings on wafers that are kept as reference, or on grating targets (known as fiducial targets) stored inside the tool. This approach involves measuring these targets with a given periodicity, and monitoring the measurement output results over time. Direct monitoring has the advantage of monitoring the tool in the most exhaustive manner, that is by directly monitoring the tool output (MCD, SWA, thickness) and on the critical layers on which the metrology system user is mostly interested. This is the method of choice in semiconductor fabrication plants (fabs): each fab chooses one or more layers, which are critical, or representative for their process; a set of reference wafers is created; the targets on those wafers are measured with a given periodicity; and the metrology results are monitored over time. Under the assumption that the targets have not changed over time, the differences in the tool output can be attributed to the tool instability.

However, there are also disadvantages with direct monitoring as described above. The monitoring interrupts tool normal operations, hence decreases availability. Where the reference grating(s) are on wafer (as it normally happens in customer fabs) there are logistical problems which might require some sort of user intervention. Where the reference grating(s) are kept on fiducial inside the tool, these are usually created by the metrology tool manufacturer, and are not necessarily compliant with the metrology tool user's interest. For instance, while the tool manufacturer may place some etched silicon gratings on the fiducial, this type of stack may not be of interest to the tool user. Also, the monitoring is intermittent and not continuous. In addition, the reference target properties might change over time; hence the user might erroneously interpret the measured difference as a change in the system rather than the target.

FIGS. 7a and 7b illustrate an embodiment of the proposed method. It is a prerequisite of this method that the tool has been properly calibrated and it is known to be in a good state. Firstly, FIG. 7a shows a flow diagram of the initial phase of the method.

In step 700, the user selects a given number of stacks and geometries (profiles) that are to be monitored.

In step 705, these stacks and geometries are modeled in the inspection apparatus, and, as a result of this action, a set of Monitoring Reference CD Profiles 710 is created.

In step 715, the full Reference Calibration Data from a given tool is collected and stored as the system Reference Calibration Data Container (RCDC). This determines the tool baseline, and contains all necessary information to make the translation from the diffraction efficiencies as calculated by the Maxwell solver to diffracted light intensities as measured by the detector (refer to element 18 in FIG. 4), including the effects of imperfections in the lenses, dust particles, scratches, illumination inhomogeneities). This makes sure that the simulated spectra (of the next step), after correction with the RCDC data, can be directly compared to the detector 18 measured data.

In step 720, using a Maxwell solver (which can be, by way of example only, a Rigorous Coupled Wave Algorithm RCWA), the user computes how the diffraction spectra for each of the Monitoring CD Profiles will look like on the selected tool. All these spectra are stored in a database, referred to hereafter as the "Monitoring Library" 725. Step 720, often called the "forward calculation", is essentially the same as step 506 (FIG. 5) and is used many times during a normal scatterometry measurement.

It should be appreciated that, during this initial phase, there is no physical measurement involved: everything is determined by modeling, and the only piece of "real" information is the Calibration Data RCDC from the tool. Also this initial phase needs only to be performed once and repeated only when the user wants (or needs, because of repair actions) to change the system baseline.

Referring now to FIG. 7b, the second phase, showing how the monitoring library 725 is used to monitor the tool, will be described.

In step 730, every day (or whenever) new Calibration Data is collected from the tool. So as to minimize data transfer, this Daily Calibration Data Container (DCDC) does not need to be a full system calibration data package, but only a subset thereof, as much of the calibration data changes only after tool recalibration. This subset may comprise the "volatile" calibration data that is always created before a measurement is taken and which is used, together with other "permanent" calibration data, to perform the measurement. In this way the daily calibration data DCDC can be a by-product of the normal tool usage. The term "permanent" calibration data is used here to identify the portion of calibration information that is determined and updated only during tool setup, periodic maintenance, or hardware recovery. The term "volatile" calibration data is used here to identify the portion of calibration information that is automatically generated by the tool on very frequent basis, in order to stay calibrated.

In step 735, and using the daily calibration data DCDC, together with the reference data RDCD collected at step 715, a CD reconstruction on the spectra stored in the Monitoring library 725 is performed with the Monitoring CD profiles 710. This CD reconstruction 735 is the normal process that is done during every scatterometry measurement and usually called "regression calculation" (described in FIG. 5, steps 506, 508, 510, 512, 514).

In step 745, the difference in the parameters between each reconstructed profile 740 and the corresponding monitoring profile 710 is computed. That is, from the CD reconstruction the user determines the MCD (mean critical dimension), SWA (side wall angle), thicknesses etc. for each profile and compares these values with the original monitoring profile used to generate the spectra in the monitoring library 725.

In step 750, the computed differences are stored to disk and can be used for trending charts 755 and further analysis.

An illustrative example of the above method is now described. Assuming a monitoring CD profile with MCD=40 nm and that the corresponding spectra have been created. If the daily calibration data DCDC collected at step 730 is the same as the RCDC collected at step 715, and this same CD profile is used, performing the reconstruction (735) on the spectra will result in the exact MCD (40 nm) which was used to create the spectra. However, if the daily calibration data DCDC collected at step 730 is different to the RCDC collected at step 715, performing the reconstruction on the spectra will result in a different MCD, for instance 41 nm. This difference represents a change in the calibration data from the initial calibration translated into CD model parameters.

In essence, for a CD reconstruction three elements are required: a CD profile, diffraction spectra, and calibration data. If the CD profile and the spectra are always the same, the changes observed in the reconstruction are due only to the calibration data and therefore the tool instability.

As an alternative to the full reconstruction described in the method above, parameter drift can be determined using the difference between the diffraction spectra calculated with the monitoring RCDC and new spectra calculated using the DCDC. This entails essentially repeating step 720 and comparing the resulting spectra to their corresponding spectra stored in the monitoring library 725. Any differences between corresponding spectra is determined by perturbations in the daily calibration data DCDC values from the monitoring RCDC. By suitably using the sensitivities of the model (derivatives of the intensities with respect to the floating parameters in the model) these perturbations in the pupil space can be translated into perturbations in the parameter space. These perturbations in the floating parameters are the values to be monitored (since they are meaningful values for the user that are directly related to the effect of the changes in the application). This approach assumes that the changes comprise small perturbations from the reference data, and is reasonably accurate provided that the changes are small enough to hold the assumption of linearity in the model. It has a main advantage of being very quick to calculate. In comparison, the full reconstruction is more time consuming but the result is closer to what is expected to be observed live on-tool, and the method allows other parameters to be monitored.

As the above, the DCDC package may comprise part of the calibration data other than that generated as part of the tool setup or recovery, and which is frequently generated/updated. This may be the data received from the inline calibrations performed before each lot/wafer measurement. Alternatively, the Daily Calibration Data can be generated on the tool as a daily scheduled task.

This strategy can be implemented on metrology systems without hardware changes and minimal software impact, as all the basic functions (libraries, forward calculations, regression calculations) used are, in many cases, already implemented in the software as part of the functionalities necessary for a normal scatterometry measurement.

In conclusion, the methods disclosed herein combine the advantages of the direct and indirect monitoring. It avoids unnecessary measurements by re-using existing data; does not require any hardware support (e.g., wafers, external tools) or user intervention; captures and translates errors in the illumination source, hardware and calibration into informative errors in parameters; and establishes an experimental framework to define thresholds for the quality of new calibrations (which may or may not imply hardware changes) within a machine and to match machine performance to a reference machine (known as a "golden machine"). It is flexible such that with the same tool input, several stacks can be simultaneously monitored. It is also robust against wafer damage: in the current approach, if a reference wafer (known as a "golden wafer") is damaged, the daily monitoring will experience an undesired jump.

Moreover, this methodology is easily extendable: it allows the user to add new monitoring profiles/stacks to the monitoring library, without influencing the tool availability (ideally, the user can monitor all the stacks used in the fab). If the daily CDC are also stored (and not deleted after usage), when a new CD profile is added to the library the user can even determine what the tool performance would have been on that profile for period of time in the past (that is in a time antecedent to the moment in which the profile is added to the monitoring library).

Even further, if the Daily CDC contains the whole tool calibration information, the method allows determination and prediction of the impact of a tool recalibration due to recovery actions.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of operating a metrology apparatus comprising:
    defining one or more first target profiles of one or more targets;
    storing initial calibration data of the metrology apparatus;
    compiling a library of modeled spectra that would be observed from inspection of the one or more targets using the metrology apparatus calibrated according to the initial calibration data;
    obtaining current calibration data of the metrology apparatus;
    modeling one or more second target profiles of the one or more targets at least partially based on the current calibration data and the library of spectra;
    determining any differences between one or more parameters of the one or more first target profiles and the one or more second target profiles; and
    using any of the determined differences between the one or more parameters to determine a drift in the one or more parameters, such that subsequent measurement stability of the metrology apparatus is improved when subsequently taking measurements of a physical target with the metrology apparatus.

2. The method of claim 1, wherein the compiling is performed using a model to determine each resultant spectra from the first target profiles.

3. The method of claim 1, wherein:
    the modeling comprises reconstructing the one or more second target profiles for one or more of the spectra compiled in the library, using the current calibration data; and the determining comprises determining differences between each second target profile and its corresponding first target profile.

4. The method of claim 1, wherein:
the modeling comprises using one or more of the first target profiles to determine further spectra that would be observed from inspection of the one or more target using the metrology apparatus calibrated according to the current calibration data; and
the determining comprises determining any differences between each of the further spectra determined in the modeling and its corresponding spectra in the library.

5. The method of claim 4, wherein the determining any differences between each of the further spectra and its corresponding spectra in the library is performed by using the sensitivities of the model(s) used to obtain the spectra to translate the calculated differences into differences between the initial calibration data and the current calibration data.

6. The method of claim 1, wherein the current calibration data is a subset of the initial calibration data.

7. The method of claim 6, wherein the current calibration data comprises measurement data generated before each lot or wafer measurement.

8. A non-transitory computer readable medium coupled to a metrology apparatus, and having stored thereon computer-executable instructions, execution of which by a processing device causes the processing device to perform operations associated with the metrology apparatus, comprising:
defining one or more first target profiles of one or more targets;
storing initial calibration data of the metrology apparatus;
compiling a library of modeled spectra that would be observed from inspection of the one or more targets using the metrology apparatus calibrated according to the initial calibration data;
obtaining current calibration data of the metrology apparatus;
modeling one or more second target profiles of the one or more targets at least partially based on the current calibration data and the library of spectra;
determining any differences between one or more parameters of the one or more first target profiles and the one or more second target profiles; and
using any of the determined differences between the one or more parameters to determine a drift in the one or more parameters, such that subsequent measurement stability of the metrology apparatus is improved when subsequently taking measurements of a physical target with the metrology apparatus.

9. A metrology apparatus comprising:
a projection system configured to project a beam of radiation onto a target; and
a processing device configured to:
define a first target profile of the target;
store initial calibration data of the metrology apparatus;
compile a library of modeled spectra that would be observed from inspection of the target using the projection system of the metrology apparatus calibrated according to the initial calibration data;
obtain current calibration data of the metrology apparatus;
model a second target profile of the target at least partially based on the current calibration data and the library of spectra;
determine any differences between one or more parameters of the first target profile and the second target profile; and
use any of the determined differences between the one or more parameters to determine a drift in the one or more parameters, such that subsequent measurement stability of the metrology apparatus is improved when subsequently taking measurements of a physical target with the metrology apparatus.

10. The metrology apparatus of claim 9, wherein the processing device is configured to compile a library of spectra using a model to determine each resultant spectra from the first target profile.

11. The metrology apparatus of claim 9, wherein the processing device is configured to:
model the second target profile by reconstructing a target profile for the spectra compiled in the library, using the current calibration data; and
determine differences between each reconstructed target profile and its corresponding first target profile.

12. The metrology apparatus of claim 9, wherein the processing device is further configured to:
use the first target profile to determine further spectra that would be observed from inspection of the target using the metrology apparatus calibrated according to the current calibration data; and
determine any differences between each of the further spectra and its corresponding spectra in the library.

13. The metrology apparatus of claim 12, wherein the processor is configured to determine any differences between each of the further spectra and its corresponding spectra in the library by using the sensitivities of the model(s) used to obtain the spectra to translate the calculated differences into differences between the initial calibration data and the current calibration data.

14. The metrology apparatus of claim 9, wherein the current calibration data is a subset of the initial calibration data.

15. The metrology apparatus of claim 14, wherein the current calibration data comprises measurement data generated before each lot or wafer measurement.

16. The metrology apparatus of claim 9, wherein the processor is configured to perform the obtaining, the modeling, and the determining every 1 to 7 days.

17. The metrology apparatus of claim 9, wherein the processor is configured to obtain the current calibration data as a daily scheduled task.

* * * * *